United States Patent
Kim (10) Patent No.: US 10,369,926 B2
(45) Date of Patent: Aug. 6, 2019

(54) DRIVER STATE SENSING SYSTEM, DRIVER STATE SENSING METHOD, AND VEHICLE INCLUDING THE SAME

(71) Applicant: Mando-Hella Electronics Corporation, Incheon (KR)

(72) Inventor: Shinwook Kim, Seoul (KR)

(73) Assignee: MANDO HELLA ELECTRONICS CORPORATION, Incheon (KR)

( * ) Notice: Subject to any disclaimer, the term of this patent is extended or adjusted under 35 U.S.C. 154(b) by 14 days.

(21) Appl. No.: 15/680,161

(22) Filed: Aug. 17, 2017

(65) Prior Publication Data
US 2018/0304806 A1  Oct. 25, 2018

(30) Foreign Application Priority Data

Apr. 25, 2017  (KR) .................. 10-2017-0052762

(51) Int. Cl.
| | |
|---|---|
| G06K 9/46 | (2006.01) |
| B60Q 9/00 | (2006.01) |
| G08B 21/06 | (2006.01) |
| G06K 9/00 | (2006.01) |
| A61B 5/00 | (2006.01) |
| A61B 5/18 | (2006.01) |
| A61B 5/11 | (2006.01) |

(52) U.S. Cl.
CPC .............. *B60Q 9/00* (2013.01); *A61B 5/0077* (2013.01); *A61B 5/1128* (2013.01); *A61B 5/18* (2013.01); *G06K 9/00845* (2013.01); *G06K 9/4604* (2013.01); *G08B 21/06* (2013.01)

(58) Field of Classification Search
CPC ........ B60Q 9/00; G08B 21/06; A61B 5/0077; A61B 5/18; A61B 5/1128; G06K 9/4604; G06K 9/00845

USPC ........................................................... 348/77
See application file for complete search history.

(56) References Cited

U.S. PATENT DOCUMENTS

| | | | |
|---|---|---|---|
| 5,729,619 A | 3/1998 | Puma | |
| 9,126,525 B2 * | 9/2015 | Lynam | B60Q 9/005 |
| 2011/0013696 A1 * | 1/2011 | Hiramatsu | H04N 19/423 |
| | | | 375/240.16 |

(Continued)

FOREIGN PATENT DOCUMENTS

| | | |
|---|---|---|
| EP | 2 343 207 | 5/2012 |
| JP | 2008-305190 | 12/2008 |
| KR | 10-0295850 | 5/2001 |

OTHER PUBLICATIONS

Jimenez-Pinto et al, Driver alert state and fatigue detection by salient points analysis (Year: 2009).*

(Continued)

*Primary Examiner* — Shan E Elahi
(74) *Attorney, Agent, or Firm* — Ladas & Parry, LLP (57) ABSTRACT

Disclosed are a driver state sensing system, a driver state sensing method, and a vehicle including the same. The driver state sensing system includes an image photographing unit composed of a single channel to photograph images, a controller that extracts at least one shape point from a driver image sensed in the images and compares a motion vector calculated based on the amount of change of the shape point with at least one drowsiness vector stored in advance to determine whether a driver is in a drowsiness state, and a warning unit to warn when it is determined that the driver is in a drowsiness state.

12 Claims, 6 Drawing Sheets

(56) References Cited

U.S. PATENT DOCUMENTS

| | | | | |
|---|---|---|---|---|
| 2012/0119064 | A1* | 5/2012 | Cieslinski | H04N 5/3653 250/208.1 |
| 2012/0212353 | A1* | 8/2012 | Fung | B60K 28/06 340/905 |
| 2013/0296660 | A1* | 11/2013 | Tsien | A61B 5/0077 600/301 |
| 2014/0139655 | A1* | 5/2014 | Mimar | G08B 21/06 348/77 |
| 2015/0071534 | A1* | 3/2015 | Riley | B60R 1/002 382/167 |
| 2015/0232065 | A1* | 8/2015 | Ricci | H04W 4/21 701/36 |
| 2015/0251602 | A1* | 9/2015 | Baur | B60R 1/00 348/148 |
| 2016/0001781 | A1* | 1/2016 | Fung | B60W 40/08 701/36 |
| 2016/0050372 | A1* | 2/2016 | Lindner | H04N 5/23267 348/46 |
| 2016/0150070 | A1* | 5/2016 | Goren | H04W 4/029 455/404.2 |
| 2016/0297365 | A1* | 10/2016 | Nix | B60R 1/002 |

OTHER PUBLICATIONS

Office Action dated Aug. 2, 2018 for Korean Patent Application No. 10-2017-0052762 and its English translation by Google Translate.

* cited by examiner

DRIVER STATE SENSING SYSTEM, DRIVER STATE SENSING METHOD, AND VEHICLE INCLUDING THE SAME

CROSS-REFERENCE TO RELATED APPLICATION(S)

This application claims the benefit of Korean Patent Application No. 2017-0052762, filed on Apr. 25, 2017 in the Korean Intellectual Property Office, the disclosure of which is incorporated herein by reference.

BACKGROUND

1. Field

The present disclosure relates to a driver state sensing system, a driver state sensing method, and a vehicle including the same, and more particularly to a driver state sensing system, a driver state sensing method, and a vehicle including the same for estimating change of a driver's gaze or head to determine whether the driver is in a drowsiness state, and to perform a warning according to the driver's drowsiness.

2. Description of the Related Art

Today, many people are injured every year due to accidents caused by drowsiness driving. In particular, when a driver of a large vehicle such as a bus or a truck drives drowsiness driving, a driver of another vehicle and even an occupant of the large vehicle may suffer damage.

Accordingly, in order to reduce traffic accidents caused by an explosive increase in the number of vehicles, a lot of efforts are being made in the development of Advanced Safety Vehicle (ASV). Technological developments in the ASV include drowsiness driving alarm systems, nighttime obstacle detection systems, vehicle hazard alarm systems and the like.

Of these, the drowsiness driving alarm systems alert a driver after detecting the drowsiness driving based on the image analysis for the driver's state such as the flicker of eyes through the CCD camera, that is, the driver's behavior, thereby obstructing drowsiness driving so that stable driving can be performed.

However, the conventional drowsiness driving alarm systems tried to recognize a driver's sleepiness or carelessness by using the biological signals such as detecting the blinking of a driver's pupil or measuring a driver's heart rate and brain wave. However, recognizing the pupil is affected by the internal illuminance of the vehicle, the brightness of the surrounding environment, the lighting condition, and the external weather. In addition, there is a problem in that it is difficult to cope with the case where the driver is wearing glasses or it is hard to recognize the pupil, such as sunglasses and the like. Accordingly, a method for detecting a driver's motion by using a stereo camera has been developed, but this method has problems that the cost incurred due to the additional mounting of the image sensor for the stereo camera configuration is increased, and a large amount of computation is consumed in the extraction of a 3D image using a stereo image, which makes real-time image processing difficult.

In addition, there is a problem that sensing the status of a driver by recognizing a biological signal is costly due to mounting the bio-signal detection device on a vehicle.

SUMMARY

Therefore, it is an aspect of the present disclosure to extract a motion of a driver by constructing a single camera, thereby minimizing an excessive amount of computation required when constructing a stereo camera.

It is another aspect of the present disclosure to minimize the problem of not only a stereo camera but also an excessive cost in detecting a state of a driver by recognizing a biological signal.

Further, it is another aspect of the present disclosure to minimize the occurrence of an accident by promptly warning a driver by learning the driver's state and determining the driver's state in real time.

Additional aspects of the present disclosure will be set forth in part in the description which follows and, in part, will be obvious from the description, or may be learned by practice of the present disclosure.

In accordance with one aspect of the present disclosure, a driver state sensing system may include an image photographing unit composed of a single channel to photograph images, a controller that extracts at least one shape point from a driver image sensed in the images and compares a motion vector calculated based on the amount of change of the shape point with at least one drowsiness vector stored in advance to determine whether a driver is in a drowsiness state, and a warning unit to warn when it is determined that the driver is in a drowsiness state.

Further, the controller may calculate a first motion vector based on a first shape point of a first frame and a second shape point of a second frame which have a time difference, in order to calculate the motion vector.

Further, the controller may include a frame buffer to store the first frame and the second frame which have a time difference.

Further, the controller may determine that a driver is in a drowsiness state and may learn the calculated motion vector if the difference between the calculated motion vector and at least one drowsiness vector stored in advance has an error smaller than a preset first threshold value.

In accordance with another aspect of the present disclosure, a driver state sensing method may include steps of photographing images based on a single-channel camera sensor, extracting at least one shape point from a driver image sensed in the images, calculating a motion vector based on the amount of change of the shape point, comparing the calculated motion vector with at least one drowsiness vector stored in advance to determine whether a driver is in a drowsiness state, and warning when it is determined that the driver is in a drowsiness state.

Further, the step of calculating a motion vector based on the amount of change of the shape point may further include storing a first shape point of a first frame, storing a second shape point of a second frame having a time difference with the first frame, and calculating the motion vector based on the first shape point and the second shape point.

Further, the step of comparing the calculated motion vector with at least one drowsiness vector stored in advance to determine whether a driver is in a drowsiness state may further include determining that the driver is in a drowsiness state if the difference between the calculated motion vector and at least one drowsiness vector stored in advance has an error smaller than a preset first threshold value.

Further, the driver state sensing method may further include a step of learning the calculated motion vector.

In accordance with another aspect of the present disclosure, a vehicle may include a driver state sensing system wherein the driver state sensing system includes an image photographing unit composed of a single channel to photograph images, a controller that extracts at least one shape point from a driver image sensed in the images and compares a motion vector calculated based on the amount of change of the shape point with at least one drowsiness vector stored in advance to determine whether a driver is in a drowsiness state, and a warning unit to warn when it is determined that the driver is in a drowsiness state.

Further, the image photographing unit includes a camera sensor of a single channel, and the camera sensor may be installed at a position of at least one of a front pillar, a rearview mirror, and a dashboard of the vehicle to photograph the driver.

Further, the controller may calculate a first motion vector based on a first shape point of a first frame and a second shape point of a second frame which have a time difference, in order to calculate the motion vector.

Further, the controller may determine that a driver is in a drowsiness state and may learn the calculated motion vector if the difference between the calculated motion vector and at least one drowsiness vector stored in advance has an error smaller than a preset first threshold value.

BRIEF DESCRIPTION OF THE DRAWINGS

These and/or other aspects of the present disclosure will become apparent and more readily appreciated from the following description of the embodiments, taken in conjunction with the accompanying drawings of which.

DETAILED DESCRIPTION

Hereinafter, embodiments of the present disclosure will be described in detail with reference to the accompanying drawings. The following embodiments are provided to fully convey the spirit of the present disclosure to a person having ordinary skill in the art to which the present disclosure belongs. The present disclosure is not limited to the embodiments shown herein but may be embodied in other forms. The drawings are not intended to limit the scope of the present disclosure in any way, and the size of components may be exaggerated for clarity of illustration.

Figure 1:
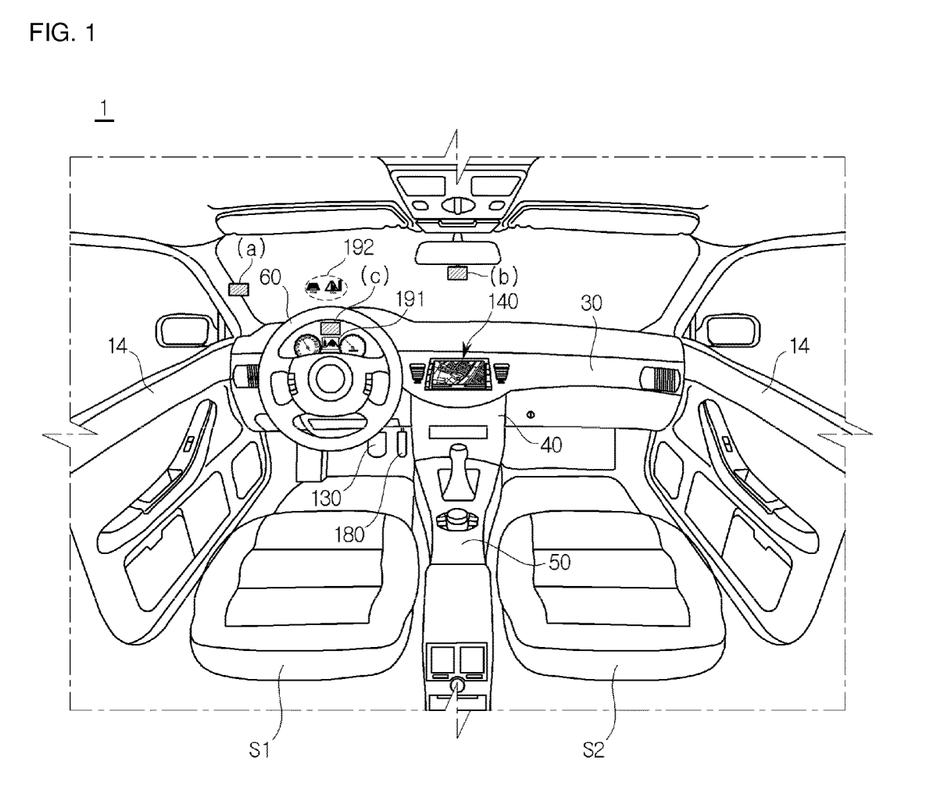
FIG. 1 is a schematic view illustrating an interior of a vehicle including a driver state sensing system according to an embodiment of the present disclosure.
Figure 2:
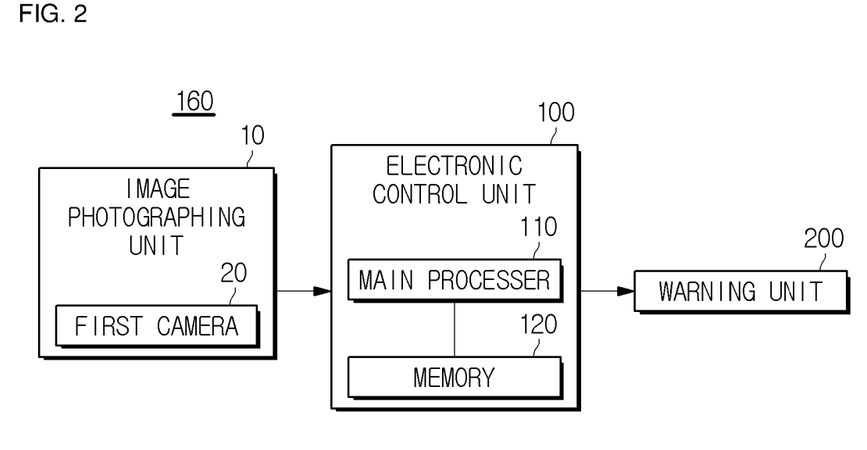
FIG. 2 is a block diagram of a driver state sensing system according to an embodiment of the present disclosure.

FIG. 1 is a schematic view illustrating an interior of a vehicle including a driver state sensing system according to an embodiment of the present disclosure, and FIG. 2 is a block diagram of a driver state sensing system according to an embodiment of the present disclosure.

As illustrated in FIG. 1, in the inside of a vehicle 1 according to this disclosure may be provided seats S1 and S2 on which occupants sit, a dash board 30 in which various instruments to control the operation of the vehicle 1 and display the driving information of the vehicle 1 are provided, a center fascia 40 provided with a control panel to operate the accessories included in the vehicle 1, a center console 50 provided with a gear stick, a parking brake stick, and the like, and a steering wheel 60 to operate the running direction of the vehicle 1.

The seats S1 and S2 allow a driver to operate the vehicle 1 in a comfortable and stable posture and may include a rear seat (not shown) located in the rear of the vehicle 1.

The dashboard 30 may be provided with an instrument panel such as a speedometer, a fuel meter, an automatic shift selector lever display, a tachometer, and an interval meter to display information related to driving. Therefore, a driver can check the current vehicle speed in real time based on the display of the speed meter or the like.

The center fascia 40 is provided between the driver's seat S1 and the front passenger's seat S2 and may include an operation unit to adjust audio equipment, an air conditioner and a heater, blowers of an air conditioner to adjust the temperature inside the vehicle bodies 11 to 16, a cigar jack, and the like.

The center console 50 is provided below the center fascia 40 between the driver's seat S1 and the front passenger's seat S2 and may be provided with a gear stick for shifting, a parking brake stick for parking, and the like.

The steering wheel 60 is attached to the dashboard 30 so as to be rotatable about a steering axis and a driver can rotate the steering wheel 60 clockwise or counterclockwise to change the traveling direction of the vehicle 1. An angle of the steering wheel 60 rotated by a driver is sensed through a steering wheel sensor (not shown) to confirm the driver's intention to change the traveling direction.

As illustrated in FIG. 1, a driver state sensing system 160 includes camera sensors (a, b and c) to sense the movement and state of a driver. Herein, not all of the camera sensors (a, b and c) are installed but one of the first camera sensor (a), the second camera sensor (b), or the third camera sensor (c) is used to photograph a driver with one channel. That is, the camera sensor may be installed at a place where observation of a driver sitting on the driver's seat S1 of the vehicle 1 is possible without being affected by the rotation of the steering wheel 60 or other obstacles.

As an example, the first camera sensor (a) may be installed on the A pillar (front pillar) which is the boundary between the front glass and the side glass of the body of the vehicle 1 toward a driver, the second camera sensor (b) may be installed on a rearview mirror toward the driver sitting in the driver's seat S1, and the third camera sensor (c) may be installed on the dashboard 30 toward the driver. However, the camera sensors are not limited to the above-described positions, may be installed in a place where the movement of the driver can be observed without being affected by the rotation of the steering wheel 60 or other obstacles and which is easy to install. That is, the camera sensor can be installed at a position where the motions of the head, neck, and shoulder of the driver can be acquired as a whole.

The configuration of the driver state sensing system 160 including the camera sensors described above will be described below with reference to FIG. 2 that is a block diagram of a driver state sensing system in accordance with an embodiment.

Referring to FIG. 2, the driver state sensing system 160 includes an image photographing unit 10, an electronic control unit 100, and a warning unit 200.

The image photographing unit 10, the electronic control unit 100, and the warning unit 200 can communicate with each other through the communication network NT of the vehicle 1. The vehicle communications network NT may employ the communication protocols of Media Oriented Systems Transport (MOST) having a communication speed of up to 24.5 Mbps (mega-bits per second), FlexRay having a communication speed of up to 10 Mbps, Controller Area Network (CAN) having a communication speed of 125 kbps (kilo-bits per second) to 1 Mbps, and Local Interconnect Network (LIN) having a communication speed of 20 kbps, and the like. Such a vehicle communication network NT may employ not only a single communication protocol such as MOST, FlexRay, CAN, and LIN but also a plurality of communication protocols.

The image photographing unit 10 includes a first camera 20. The first camera 20 can photograph a state of a driver who is driving in the driver's seat using a one-channel camera. The first camera 20 may be employed as one of the first camera sensor a, the second camera sensor b, and the third camera sensor c shown in FIG. 1.

Further, the first camera 20 may usually use CMOS as its image sensor. A CMOS image sensor is a semiconductor memory device that converts an exposed image into an electrical form and transmits it. Further, the first camera 20 may employ an RGB sensor, an infrared image sensor, or the like.

Therefore, the images acquired by the first camera 20 can be transmitted to the electronic control unit 100.

The electronic control unit 100, which collectively controls the driver state sensing system 160, includes a main processor 110 to determine a state of a driver based on an image acquired by the image photographing unit 10 hardware-wise and a memory 120 to store various data.

The memory 120, which stores the programs and data of the driver state sensing system 160, may include a nonvolatile memory such as a flash memory, a read only memory (ROM), an erasable programmable read only memory (EPROM), and an electrically erasable programmable read only memory (EEPROM), as well as a volatile memory such as an S-RAM or a D-RAM.

The nonvolatile memory can semi-permanently store control programs and control data for controlling the operation of the driver state sensing system 160, and the volatile memory can retrieve and temporarily stores the control programs and the control data from the nonvolatile memory, and temporarily stores driver image information sensed by the image photographing unit 10 and various control signals outputted from the main processor 110.

Hereinafter, a method of sensing the driver's drowsiness state in the electronic control unit 100 of the driver state sensing system 160 illustrated in FIG. 3 will be described.

First, a calculation unit 130 generates a motion vector v from the image information received from the image photographing unit 10.

The calculation unit 130 performs a difference comparison operation between the N−1 [sec] viewpoint frame and the N [sec] viewpoint frame which are obtained by the image photographing unit 10 in order to generate the motion vector v. That is, the calculation unit 130 extracts a shape point from the image frames transmitted from the image photographing unit 10, and generates a comparison object.

Herein, the shape point is also referred to as a feature point.

Figure 4A:
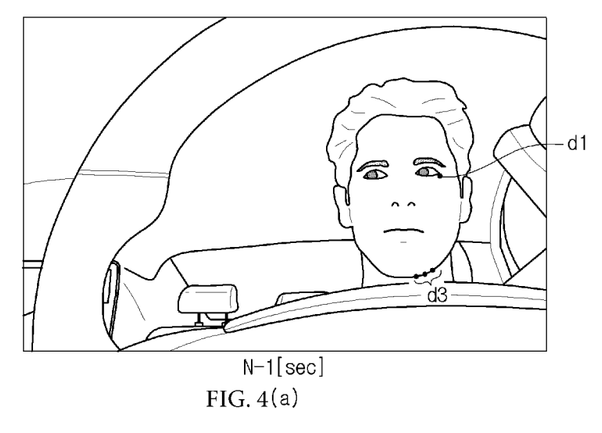
FIG. 4*a* is a schematic view illustrating an image at N−1 [sec] acquired by an image photographing unit according to an embodiment of the present disclosure.
Figure 4B:
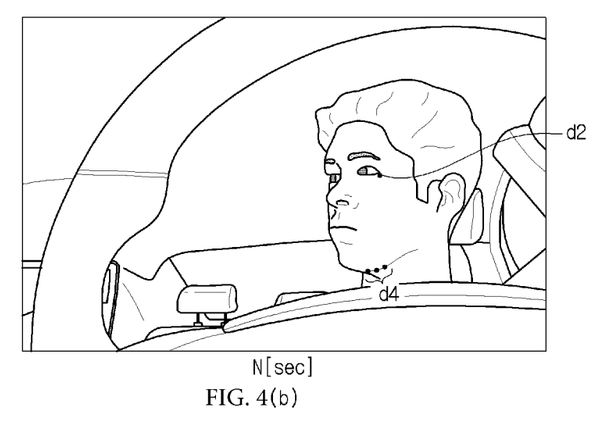
FIG. 4*b* is a schematic view illustrating an image at N[sec] acquired by an image photographing unit according to an embodiment of the present disclosure.

As an example, as illustrated in FIG. 4, by extracting the driver' pupil from an image of the N−1 [sec] viewpoint as a first shape point d1 at the N−1 [sec] viewpoint and extracting the driver' pupil from an image of the N [sec] viewpoint as a second shape point d2 at the N [sec] viewpoint, the first motion vector v1 can be generated based on the first shape point and the second shape point.

Further, as another example, as illustrated in FIG. 4, by extracting the driver's jaw portion from an image of the N−1 [sec] viewpoint as a third shape point d3 at the N−1 [sec] viewpoint and extracting the driver's jaw portion from an image of the N [sec] viewpoint as a fourth shape point d4 at the N [sec] viewpoint, the second motion vector v2 can be generated based on the third shape point and the fourth shape point.

As such, the calculation unit 130 may extract not only the driver' pupil but also a plurality of shape points from an image in order to sense changes in the body movements of the driver's head, neck, shoulders, and the like.

Herein, the calculation unit 130 may use a Scale-Invariant Feature Transform (SIFT), a Speed-Up Robust Feature (SURF), or an AKAZE algorithm, which perform detection of feature points and technique of feature amounts to find strong feature points in image rotation, scale change, illumination change, and the like, as Image processing techniques for extracting shape points.

Accordingly, the memory 120 of the electronic control unit 100 includes a frame buffer capable of storing image data of at least two frames in order to perform a difference comparison operation between frames having a time difference in the calculation unit 130.

Therefore, the calculation unit 130 can estimate the change of the driver's gaze and the vertical or horizontal change of the driver's head based on the size and direction of the motion vector v1. Further, the calculation unit 130 can estimate the driver's gaze change and the vertical or horizontal change of the driver's head based on a plurality of motion vectors generated based on the change of a plurality of shape points in one image.

Next, a determination unit 140 analyzes the calculated motion vector v.

First, the determination unit 140 performs a filtering process for determining the motion vector v determined to be not the motion of the driver in the driver's seat as noise, considering the direction and size of the calculated motion vector v. Further, if the motion vector v is a motion that is smaller than a preset motion, the determination unit 140 also excludes the motion vector from the driver recognition object through the filtering process.

Further, the determination unit 140 may exclude the vector from the driver recognition object through the filtering process, if the motion vector v includes a vector component that is out of an angle within a preset range.

Next, the determination unit 140 calculates a relative distance between the two vectors through the method of pattern matching, etc. with the motion vectors of a drowsiness state stored in a learning unit 150 in advance. In particular, the determination unit 140 continues the process of finding the motion vector having a minimum relative distance by performing pattern matching multiple times with a plurality of patterns stored in advance in the learning unit 150.

Accordingly, when the motion vector determined by performing pattern matching a plurality of times is calculated to have a relative distance smaller than a predefined threshold value, the determination unit 140 determines that the driver is in a drowsiness state.

Further, in a case where a plurality of motion vectors are present, the determination unit 140 may determine that the driver is in a drowsiness state when all of the plurality of motion vectors are calculated to have a relative distance smaller than a predefined threshold value. However, the predefined threshold value to be compared by the determination unit 140 may be set to a relatively large value, thereby preventing a case where it is determined unnecessarily as a drowsiness driving.

Further, the determination unit 140 further stores an obtained motion vector in the learning unit 150 when it is determined that the obtained motion vector can represent a new type of drowsiness state.

That is if the motion vector acquired by the determination unit 140 does not exist in the existing drowsiness pattern database, the learning unit 150 can perform learning by adding the motion vector to the database as a new type of drowsiness driving pattern. The learning unit 150 which is included in the memory 120 described with reference to FIG. 2, may be stored in a flash memory, a read only memory (ROM), an erasable programmable read only memory (EPROM), an electrically erasable programmable read only memory (EEPROM) and the like which are a nonvolatile memory.

Figure 3:
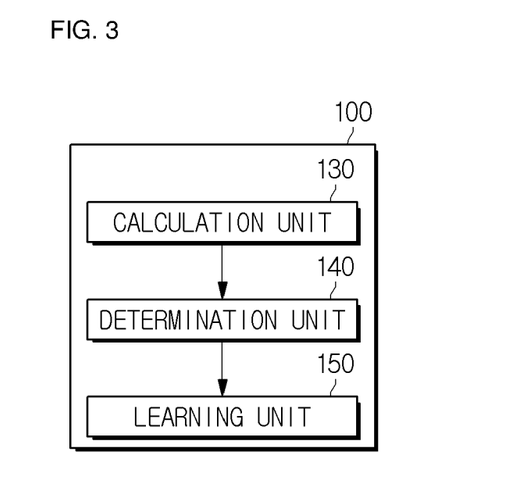
FIG. 3 is an internal block diagram of an electronic control unit included in a driver state sensing system according to an embodiment of the present disclosure.

Further, as illustrated in FIG. 3, the driver state sensing system 160 may include, as software, the calculation unit 130 to calculate a motion vector of a driver based on an image acquired by the image photographing unit 10, the determination unit 140 to determine whether the driver is in a drowsiness state based on the motion vector calculated by the calculation unit 130, and the learning unit 150 to learn and store the acquired image information as data for determining whether the driver is in a drowsiness state.

Next, when the determination unit 140 determines that the driver is in a drowsiness state, the warning unit 200 can operate various devices of the vehicle 1 so that the driver can escape from the drowsiness state by giving a vibration to the steering wheel 60 of the vehicle 1, by venturing the driver's attention by an alarm output through a speaker (not shown) included in the vehicle 1, or by opening windows, etc.

As above, the configuration of the driver state sensing system 160 according to the present disclosure has been described.

Hereinafter, the operation of the driver state sensing system 160 according to the present disclosure will be described with reference to FIGS. 5 and 6, which are flowcharts illustrating a driver state sensing method.

Figure 5:
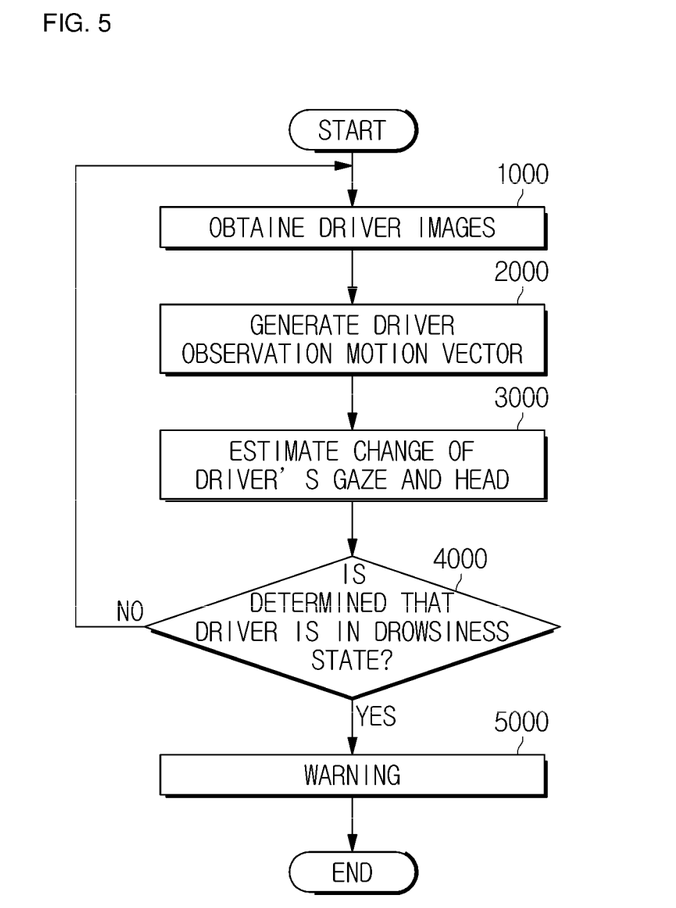
FIG. 5 is a flowchart illustrating a driver state detection method according to an embodiment of the present disclosure.
Figure 6:
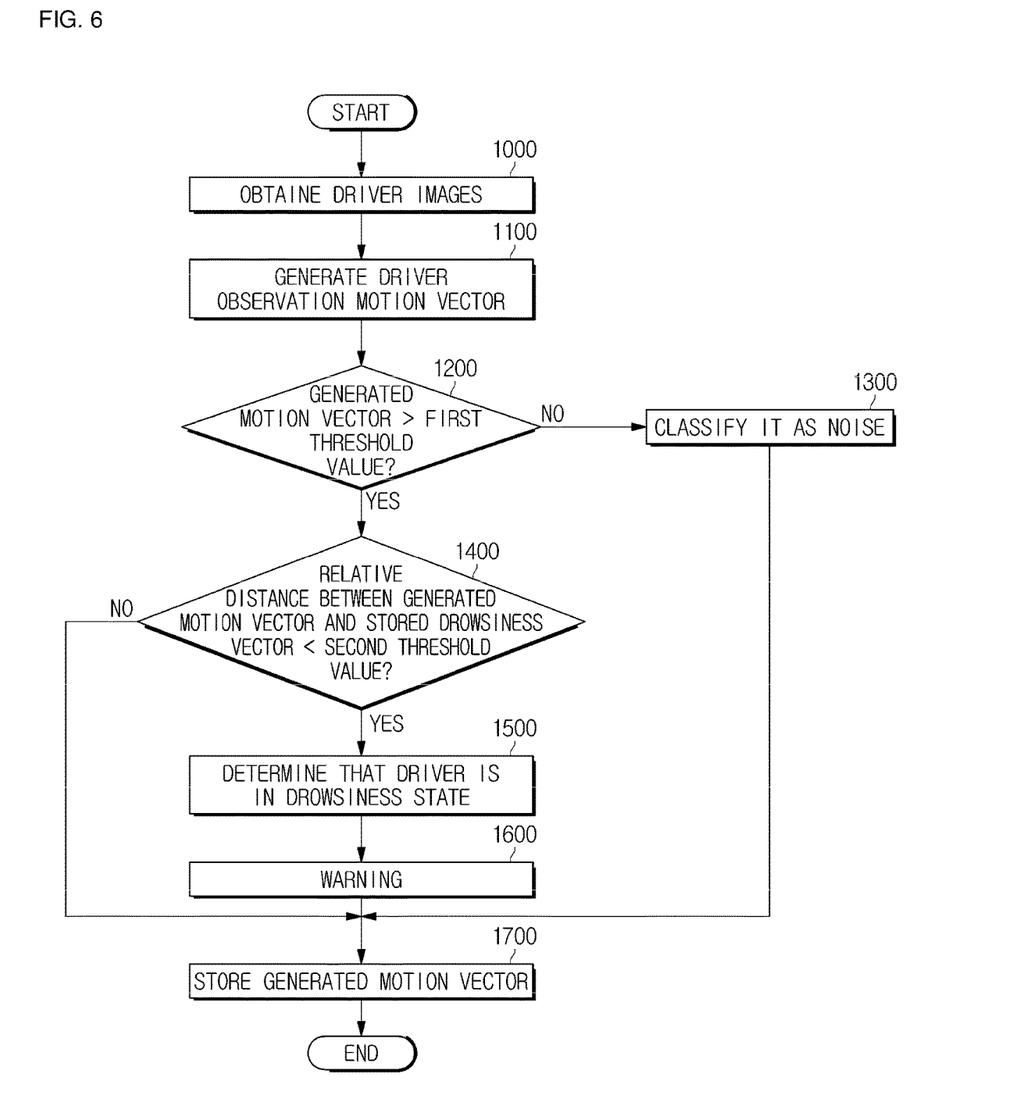
FIG. 6 is a flowchart illustrating a driver slate detection method according to another embodiment of the present disclosure.

First, as illustrated in FIG. 5, the driver state sensing system 160 acquires a driver image (1000). Specifically, the first camera 20 included in the image photographing unit 10 may acquire an image including the driver.

Then, the driver state sensing system 160 generates a motion vector v based on the acquired images. Especially, in order to generate the motion vector v, the calculation unit 130 in the electronic control unit 100 may extract a shape point and calculate the motion vector v based on the shape point.

Thereafter, the calculation unit 130 estimates the change of the driver's gaze and head based on the calculated motion vector v (3000). For example, the calculation unit 130 may analyze a motion vector calculated by using the pupil as a shape point in order to estimate the driver's gaze change, and may analyze motion vectors obtained by using the jaw portion of the driver's face as a plurality of shape points to estimate the driver's head change.

Accordingly, if the determination unit 140 determines that the driver is in a drowsiness state (YES in step 4000) based on the change of the driver's gaze and head and the like estimated by the calculation unit 130, the drowsiness warning is performed to the driver through the warning unit 200 (5000).

If the determination unit 140 determines that the driver is not in a drowsiness state (NO in step 4000) based on change of the driver's gaze and head and the like estimated by the calculation unit 130, the driver's image is continuously acquired in order to determine the driver's drowsiness state (1000).

Hereinafter, a method of estimating the driver's gaze or head change based on the motion vector generation as in FIG. 5 will be described in detail with reference to FIG. 6.

First, the driver state sensing system 160 acquires a driver image as in FIG. 5 (1000). Then, based on the acquired image, the driver state sensing system 160 generates a motion vector v (1100).

Thereafter, when performing the analysis on the basis of the size and the direction of the generated motion vector v, the driver state sensing system 160 classifies the motion vector as noise if the generated motion vector is smaller than the first threshold value (NO in step 1200). That is, if the motion vector v is a motion of a degree (first threshold value) smaller than a preset motion, the determination unit 140 also excludes the motion vector from the driver recognition object through a filtering process. Accordingly, the motion vector v classified as noise is also stored as learning data that can be classified as noise thereafter (1700).

When performing the analysis on the basis of the size and the direction of the generated motion vector v, the driver state sensing system 160 calculates the relative distance between the generated motion vector and the stored drowsiness vector if the generated motion vector is larger than the first threshold value (YES in step 1200).

At this time, the driver state sensing system 160 determines that the driver is in a drowsiness state (1600) if the calculated relative distance is smaller than a preset second threshold value (YES in step 1400).

Accordingly, when it is determined that the driver is in a drowsiness state, the driver state detection system 160 alerts the driver (1600) and stores the motion vector as learning data for determining the drowsiness state thereafter (1700).

Further, the driver state sensing system 160 determines that the driver is not in a drowsiness state (1600) if the calculated relative distance is greater than the preset second threshold value (NO in step 1400), and stores the motion vector as learning data for determining the non-drowsiness state thereafter (1700).

As is apparent from the above, the present disclosure has the effect that an excessive amount of calculation required when a stereo camera is used is not required by extracting the motion of a driver with a single camera.

Further, the present disclosure has an effect of not requiring an excessive cost incurred in recognizing a biological signal to detect a driver's state as well as a cost of a stereo camera.

Further, the present disclosure has an effect of preventing an accident from occurring by immediately warning by learning a state of a driver and determining the state of the driver in real time.

Although the present disclosure has been described with reference to an embodiment illustrated in the accompanying drawings, it will be understood by those skilled in the art that it is only illustrative, and various changes and modifications may be made without departing from the scope of the present disclosure. Accordingly, the true scope of the present disclosure should be determined only by the appended claims.

What is claimed is:

1. A driver state sensing system comprising:
an image photographing unit comprising a channel to photograph images;
a controller that extracts at least two shape points from driver images sensed in the images and compares a motion vector calculated based on an amount of change of the shape points with at least one drowsiness vector stored in advance to determine whether a driver is in a drowsiness state; and
a warning unit to warn when it is determined that the driver is in a drowsiness state.

2. The driver state sensing system according to claim 1, wherein the controller calculates the motion vector based on a first shape point of a first frame captured at a first time and a second shape point of a second frame captured a second time which is different from the first time.

3. The driver state sensing system according to claim 2, wherein the controller comprises a frame buffer to store the first frame of the first time and the second frame of the second time.

4. The driver state sensing system according to claim 1, wherein the controller determines that a driver is in the drowsiness state and learns the calculated motion vector if difference between the calculated motion vector and the at least one drowsiness vector stored in advance has an error smaller than a preset first threshold value.

5. A driver state sensing method comprising:
photographing images based on a camera sensor;
extracting at least two shape points from driver images sensed in the images;
calculating a motion vector based on an amount of change of the shape points;
comparing the calculated motion vector with at least one drowsiness vector stored in advance to determine whether a driver is in a drowsiness state; and
warning when it is determined that the driver is in the drowsiness state.

6. The driver state sensing method according to claim 5, wherein the calculating the motion vector comprises:
storing a first shape point of a first frame captured at a first time;
storing a second shape point of a second frame captured at a second time which is different from the first time; and
calculating the motion vector based on the first shape point and the second shape point.

7. The driver state sensing method according to claim 5, wherein the comparing the calculated motion vector with the at least one drowsiness vector comprises:
determining that the driver is in the drowsiness state if difference between the calculated motion vector and the at least one drowsiness vector stored in advance has an error smaller than a preset first threshold value.

8. The driver state sensing method according to claim 7, further comprising learning the calculated motion vector.

9. A vehicle comprising a driver state sensing system,
wherein the driver state sensing system comprises:
an image photographing unit comprising a channel to photograph images;
a controller that extracts at least two shape points from driver images sensed in the images and compares a motion vector calculated based on an amount of change of the shape points with at least one drowsiness vector stored in advance to determine whether a driver is in a drowsiness state; and
a warning unit to warn when it is determined that the driver is in the drowsiness state.

10. The vehicle according to claim 9,
wherein the image photographing unit comprises a camera sensor, and
the camera sensor is installed at a position of at least one of a front pillar, a rearview mirror, and a dashboard of the vehicle to photograph the driver.

11. The vehicle according to claim 10,
wherein the controller calculates the motion vector based on a first shape point of a first frame captured at a first time and a second shape point of a second frame captured at a second time which is different from the first time.

12. The vehicle according to claim 11,
wherein the controller determines that the driver is in the drowsiness state and learns the calculated motion vector if the difference between the calculated motion vector and the at least one drowsiness vector stored in advance has an error smaller than a preset first threshold value.

* * * * *